(12) United States Patent
Melder (10) Patent No.: US 12,226,142 B2
(45) Date of Patent: **\*Feb. 18, 2025**

(54) DEVICES, AGENTS, AND ASSOCIATED METHODS FOR SELECTIVE MODULATION OF RENAL NERVES

(71) Applicant: Medtronic Ireland Manufacturing Unlimited Company, Dublin (IE)

(72) Inventor: Robert J. Melder, Santa Rosa, CA (US)

(73) Assignee: Medtronic Ireland Manufacturing Unlimited Company, Dublin (IE)

( * ) Notice: Subject to any disclaimer, the term of this patent is extended or adjusted under 35 U.S.C. 154(b) by 742 days.

This patent is subject to a terminal disclaimer.

(21) Appl. No.: 17/461,449

(22) Filed: Aug. 30, 2021

(65) Prior Publication Data

US 2021/0386469 A1    Dec. 16, 2021

Related U.S. Application Data

(63) Continuation of application No. 16/250,312, filed on Jan. 17, 2019, now Pat. No. 11,116,561.
(Continued)

(51) Int. Cl.
| | |
|---|---|
| *A61B 18/06* | (2006.01) |
| *A61K 9/00* | (2006.01) |
| *A61K 31/165* | (2006.01) |
| *A61K 47/64* | (2017.01) |
| *A61M 37/00* | (2006.01) |
| *A61P 13/12* | (2006.01) |

(Continued)

(52) U.S. Cl.
CPC ............ *A61B 18/06* (2013.01); *A61K 9/0019* (2013.01); *A61K 9/0034* (2013.01); *A61K 31/165* (2013.01); *A61K 47/64* (2017.08); *A61M 37/00* (2013.01); *A61P 13/12* (2018.01); *A61P 25/00* (2018.01); *C12Y 302/01017* (2013.01); *A61B 2018/0022* (2013.01); *A61B 2018/00404* (2013.01); *A61B 2018/00434* (2013.01); *A61B 2018/00511* (2013.01); *A61B 2018/00577* (2013.01); *A61M 2025/1015* (2013.01); *A61M 2025/1052* (2013.01)

(58) Field of Classification Search
CPC .. A61M 2025/1015; A61M 2025/1052; C12Y 302/01017
See application file for complete search history.

(56) References Cited

U.S. PATENT DOCUMENTS

| | | | |
|---|---|---|---|
| 2002/0016565 A1* | 2/2002 | Zadno-Azizi | A61M 25/0054 604/101.03 |
| 2015/0133850 A1* | 5/2015 | Tunev | A61B 18/02 606/41 |

FOREIGN PATENT DOCUMENTS

| | | | | |
|---|---|---|---|---|
| WO | WO-9933407 A1 * | 7/1999 | | A61B 17/12045 |

\* cited by examiner

*Primary Examiner* — Emily L Schmidt
*Assistant Examiner* — Samuel J Marrison
(74) *Attorney, Agent, or Firm* — Shumaker & Sieffert, P.A.

(57) ABSTRACT

Devices, agents, and associated methods for selective modulation of renal nerves by localized delivery of neural ablative substances are disclosed herein. One aspect of the present technology is directed to a method for delivering a neuromodulatory agent (e.g., capsaicin) via a catheter to a kidney of the patient. The neuromodulatory agent selectively neuromodulates afferent renal nerves in a patient compared efferent renal nerves of the patient. The method can also include removing the catheter from the patient after delivering the neuromodulatory agent to conclude the procedure.

20 Claims, 8 Drawing Sheets

Related U.S. Application Data

(60) Provisional application No. 62/606,157, filed on Apr. 20, 2018, provisional application No. 62/621,407, filed on Jan. 24, 2018.

(51) Int. Cl.
*A61P 25/00* (2006.01)
*A61B 18/00* (2006.01)
*A61M 25/10* (2013.01)

DEVICES, AGENTS, AND ASSOCIATED METHODS FOR SELECTIVE MODULATION OF RENAL NERVES

CROSS-REFERENCE

This application is a continuation of U.S. patent application Ser. No. 16/250,312, filed Jan. 17, 2019, which claims the benefit of U.S. Provisional Patent Application No. 62/621,407, filed Jan. 24, 2018, and U.S. Provisional Patent Application No. 62/606,157, filed Apr. 20, 2018, the disclosures of each of which are incorporated herein by reference in their entireties.

TECHNICAL FIELD

The present technology relates generally to the modulation of renal nerves. In particular, several embodiments are directed to devices, agents, and associated methods for selective modulation of renal nerves by localized delivery of neural ablative substances.

BACKGROUND

The sympathetic nervous system (SNS) is a primarily involuntary bodily control system typically associated with stress responses. Fibers of the SNS extend through tissue in almost every organ system of the human body and can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (e.g., heart failure), and progressive renal disease.

Sympathetic nerves of the kidneys terminate in the renal blood vessels, the juxtaglomerular apparatus, and the renal tubules, among other structures. Stimulation of the renal sympathetic nerves can cause, for example, increased renin release, increased sodium reabsorption, and reduced renal blood flow. These and other neural-regulated components of renal function are considerably stimulated in disease states characterized by heightened sympathetic tone. For example, reduced renal blood flow and glomerular filtration rate as a result of renal sympathetic efferent stimulation is likely a cornerstone of the loss of renal function in cardio-renal syndrome, (i.e., renal dysfunction as a progressive complication of chronic heart failure). Pharmacologic strategies to thwart the consequences of renal sympathetic stimulation include centrally-acting sympatholytic drugs, beta blockers (e.g., to reduce renin release), angiotensin-converting enzyme inhibitors and receptor blockers (e.g., to block the action of angiotensin II and aldosterone activation consequent to renin release), and diuretics (e.g., to counter the renal sympathetic mediated sodium and water retention). These pharmacologic strategies, however, have significant limitations including limited efficacy, compliance issues, side effects, and others.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

DETAILED DESCRIPTION

The present technology is generally directed to devices, agents, and associated methods for selective modulation of renal nerves by localized delivery of neural ablative substances. In certain embodiments, the current approach includes methods for selectively ablating nerve axons within the kidney. The disclosed methods are expected to help minimize or eliminate potential injury to renal vasculature, perivascular tissue, and non-renal nerves leading to organs other than the kidney during renal denervation therapy.

Specific details of several embodiments of the present technology are described herein with reference to FIGS. 1-9. Although many of the embodiments are described with respect to devices, systems, agents, and methods for intravascular renal neuromodulation, other applications and other embodiments in addition to those described herein are within the scope of the present technology. For example, at least some embodiments may be useful for intravascular neuromodulation, for non-renal neuromodulation, and/or for use in therapies other than neuromodulation. In addition, embodiments of the present technology can have different configurations, components, and/or procedures than those shown or described herein. Moreover, a person of ordinary skill in the art will understand that embodiments of the present technology can have configurations, components, and/or procedures in addition to those shown or described herein, and that these and other embodiments can be without several of the configurations, components, and/or procedures shown or described herein without deviating from the present technology.

As used herein, the terms "distal" and "proximal" define a position or direction with respect to a clinician or a clinician's control device (e.g., a handle of a neuromodulation device). The terms, "distal" and "distally" refer to a position distant from or in a direction away from a clinician or a clinician's control device. The terms "proximal" and "proximally" refer to a position near or in a direction toward a clinician or a clinician's control device. The headings provided herein are for convenience only and should not be construed as limiting the subject matter disclosed.

Selective Renal Neuromodulation

The kidneys are innervated with both afferent and efferent nerves. The afferent renal nerves carry signals from the kidneys to the central nervous system, and the efferent renal nerves carry signals from the central nervous system to the kidneys. Positive outcomes have been reported from neuromodulation of both the afferent and efferent renal nerves. Afferent and efferent renal nerves can affect the progression of disease states (e.g., hypertension) associated with systemic sympathetic overactivity or hyperactivity in different ways. For example, efferent renal nerves can affect sodium reabsorption, rennin release, and renal blood flow, while afferent renal nerves can affect the centrally-mediated sympathetic nervous system. As evidenced by positive, long-term outcomes in kidney transplant patients, both afferent and efferent communication with the kidneys can be disabled in some cases without serious complications. Much of the functionality of efferent renal nerves, for example, can be redundant to other bodily systems. Accordingly, some approaches to renal neuromodulation can be non-selective with respect to afferent and efferent renal nerves. For example, modulation of a renal plexus via a renal artery access typically affects both afferent and efferent renal nerves.

Different strategies have been employed to ablate nerves communicating with the kidneys in an attempt to produce a therapeutic impact on pathologies such as hypertension, atrial fibrillation, and local pain associated with renal pathologies. These approaches have involved direct surgical interdiction of regional nerves, with or without topical application of neurotoxic agents, intraarterial application of energy to heat the periarterial tissue, cryogenic treatment to freeze tissues and thermally ablate the associated nerves, or local injection of neurotoxic agents to the peri-arterial regions. All of these methods rely upon producing a lethal injury to a nerve axon at some point along it length, resulting in the eventual death of the entire axon. These approaches generally do not discriminate between afferent (sensory) and efferent (sympathetic) neurons in a treated nerve bundle. There can be reasons, however, to modulate afferent or efferent renal nerves selectively.

Selective renal neuromodulation can include modulating afferent renal nerves preferentially over efferent renal nerves or modulating efferent renal nerves preferentially over afferent renal nerves. Complete selectivity is not necessary, but rather several embodiments include modulating one of the efferent or afferent renal nerves to a greater extent than the other. Kidneys typically include a greater number of efferent nerves than afferent nerves, so selective modulation of afferent renal nerves can still involve modulating a greater number of efferent renal nerves than afferent renal nerves in several embodiments. For example, a treatment procedure for selective modulation of afferent renal nerves can modulate a greater percentage of the total afferent renal nerves of a kidney and a lower percentage of the total efferent renal nerves of the kidney. Similarly, selective modulation of efferent renal nerves can modulate a greater percentage of the total efferent renal nerves of a kidney and a lower percentage of the total afferent renal nerves of the kidney. In some embodiments of treatment procedures in accordance with the present technology, selective modulation of afferent renal nerves can include modulating greater than about 50% (e.g., greater than about 60% or greater than about 70%) of the total afferent renal nerves of a kidney and less than about 50% (e.g., less than about 40% or less than about 30%) of the total efferent renal nerves of the kidney. Similarly, an embodiment of a treatment procedure for selective modulation of efferent renal nerves can include modulating greater than about 50% (e.g., greater than about 60% or greater than about 70%) of the total efferent renal nerves of a kidney and less than about 50% (e.g., less than about 40% or less than about 30%) of the total afferent renal nerves of the kidney.

In some cases, certain disease states can be associated with higher activity of afferent renal nerves compared to the activity of efferent renal nerves, while other disease states are associated with higher activity of efferent renal nerves than with the activity of afferent renal nerves. For example, selective modulation of one of afferent and efferent renal nerves can have a greater effect on some or all disease states associated with systemic sympathetic overactivity or hyperactivity than selective modulation of the other. In some cases, selective modulation of afferent renal nerves can have a greater effect on renal conditions (e.g., polycystic kidney disease) than selective modulation of efferent renal nerves. Furthermore, with respect to certain disease states, selective renal neuromodulation can provide some of, most of, all of, or more than the beneficial effect of non-selective renal neuromodulation. For example, selective modulation of afferent renal nerves can be therapeutically effective for the treatment of erectile dysfunction about equally or to a greater extent than non-selective renal neuromodulation.

Neuromodulation selective to one of the afferent or efferent renal nerves can cause less disruption of normal renal-nerve activity than non-selective renal neuromodulation. Preserving more functionality of one of the afferent or efferent renal nerves compared to nonselective renal neuromodulation can have specific utility. For example, preserving some or all renal afferent functionality can be useful to reduce the possibility of late detection of kidney stones that would otherwise have been detectable earlier due to a pain response carried by afferent renal nerves. This can be particularly useful in patients diagnosed as having cystinuria or as having an increased risk of developing kidney stones relative to the general population, e.g., based on a familial history of kidney stones. Preserving renal efferent functionality can be useful, for example, in patients having an inability or a reduced ability to compensate for missing renal efferent functionality with other bodily systems.

Selective renal neuromodulation in accordance with embodiments of the present technology can include preferentially targeting one of the afferent or efferent renal nerves over the other based on selection of a neuromodulatory agent. The disclosed neuromodulatory agents, for example, have selective neurotoxicity impacting one type of nerve axon, but not another. Further details are described below with reference to FIGS. 1-3.

Selected Examples of Renal Neuromodulation Systems

Figure 1:
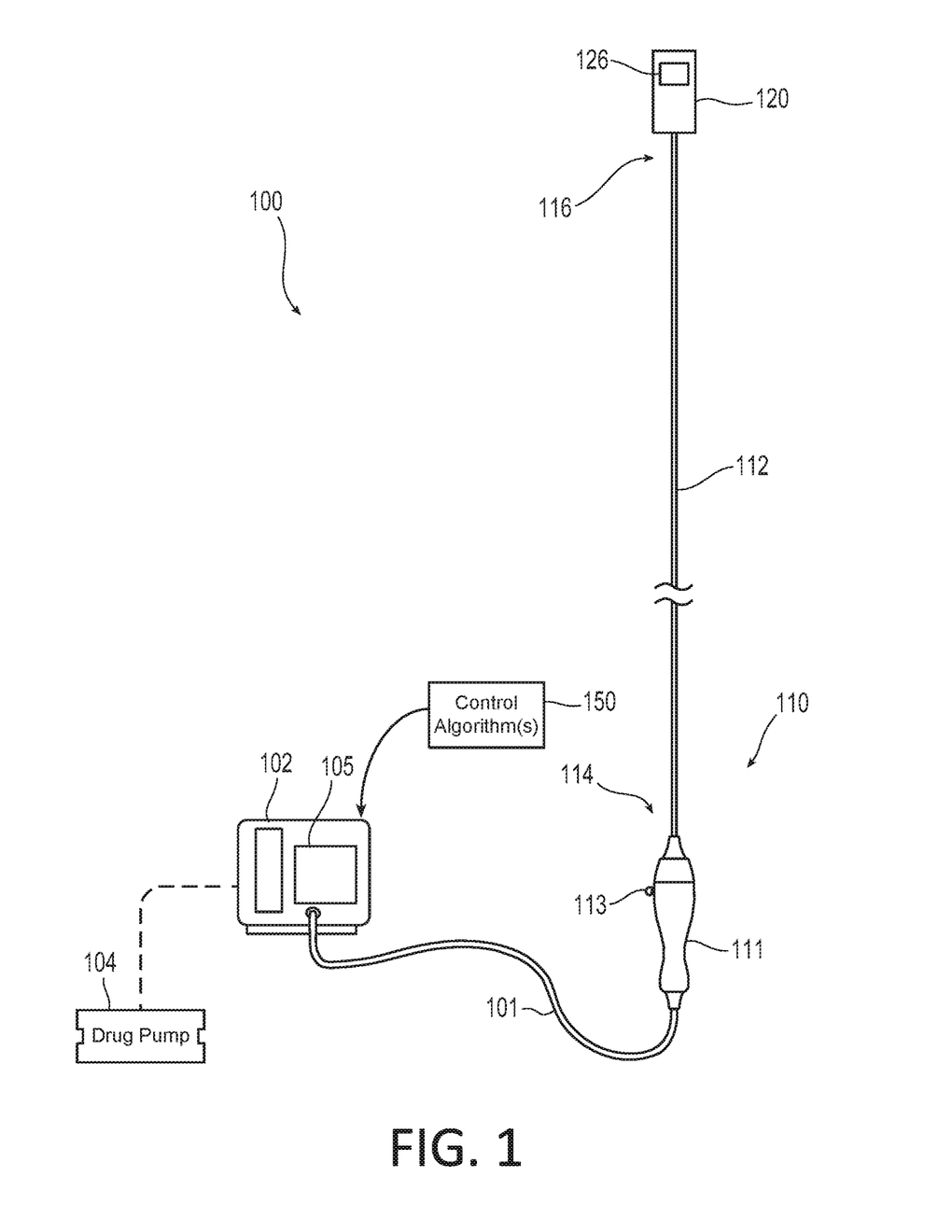
FIG. 1 is a partially-schematic view illustrating a renal neuromodulation system configured in accordance with an embodiment of the present technology.

FIG. 1, for example, is a partially schematic illustration of a renal neuromodulation system ("system 100") configured for selective modulation of renal nerves in accordance with an embodiment of the present technology. As shown in FIG. 1, the system includes a neuromodulation catheter 110, a console 102, and a cable or lead 116 extending therebetween. The neuromodulation catheter 110 can include an elongated shaft 112 having a proximal portion 114, a distal portion 116, a handle 111 operably connected to the shaft 111 at the proximal portion 114, and a neuromodulation assembly 120 operably connected to the shaft 112 at the distal portion 116. The shaft 112 and the neuromodulation assembly 120 can be 2, 3, 4, 5, 6, or 7 French or another suitable size. As shown schematically in FIG. 1, the neuromodulation assembly 120 (shown schematically) can include a neuromodulatory drug or agent delivery element 126 configured for intravascular delivery of a selected drug/agent during a treatment procedure. Further details regarding delivery of the neuromodulatory agent are described below.

The distal portion 116 of the shaft 112 is configured to be moved within a lumen of a human patient and locate the neuromodulation assembly 120 at a target site within or otherwise proximate to the lumen. For example, the shaft 112 can be configured to position the neuromodulation assembly 120 within a blood vessel, a duct, an airway, or another naturally occurring lumen within the human body. In certain embodiments, intravascular delivery of the neuromodulation assembly 120 includes percutaneously inserting a guide wire (not shown) into a body lumen of a patient and moving the shaft 112 and/or the neuromodulation assembly 120 along the guide wire until the neuromodulation assembly 120 reaches a target site (e.g., a renal artery, a renal vein). For example, the distal end of the neuromodulation assembly 120 may define a passageway for engaging the guide wire for delivery of the neuromodulation assembly 120 using over-the-wire (OTW) or rapid exchange (RX) techniques. In other embodiments, the neuromodulation catheter 110 can be a steerable or non-steerable device configured for use without a guide wire. In still other embodiments, the neuromodulation catheter 110 can be configured for delivery via a guide catheter or sheath (not shown).

The neuromodulation assembly 120 can have a single state or configuration, or it can be convertible between a plurality of states or configurations for delivery of the neuromodulatory agent. For example, the neuromodulation assembly 120 can be configured to be delivered to a treatment location in a delivery state and to provide or support therapeutically-effective, renal neuromodulation in a deployed or expanded state. In these and other embodiments, the neuromodulation assembly 120 can have different sizes and/or shapes in the delivery and deployed states. The neuromodulation assembly 120 can be converted (e.g., placed or transformed) between the delivery and deployed states via remote actuation, e.g., using an actuator 113 of the handle 111. The actuator 113 can include a knob, a pin, a lever, a button, a dial, or another suitable control component. The neuromodulation assembly 120 may also include one or more balloons or expandable members adapted to expansion at a target site within the patient. In other embodiments, the neuromodulation assembly 120 can be transformed between the delivery and deployed states using other suitable mechanisms or techniques.

As noted previously, the neuromodulation assembly 120 is configured for intravascular, extravascular, transvascular, and/or transluminal delivery of neuromodulatory drugs, agents, and/or chemicals. For example, the neuromodulation assembly 120 can include one or more openings (not shown), and chemicals (e.g., drugs or other agents) can be deliverable through the openings. For transvascular or transluminal delivery, the neuromodulation assembly 120 can include one or more needles (not shown) (e.g., retractable needles) and the openings can be at end portions of the needles.

The console 102 can be configured to control, monitor, supply, or otherwise support operation of the neuromodulation assembly 120. For example, the console 102 can include a chemical reservoir (not shown) and can be configured to supply the neuromodulation assembly 120 with one or more drugs, agents, and/or chemicals via drug pump 104.

The console 102 can be configured to execute an automated control algorithm and/or to receive control instructions from operation of the neuromodulation assembly 120. Furthermore, the console 102 can be configured to provide feedback to an operator before, during, and/or after a treatment procedure via a display 105. In some embodiments, the console 106 can include a processing device (not shown) having processing circuitry, e.g., a microprocessor. The processing device can be configured to execute stored instructions relating to a control algorithm 150. Furthermore, the console 102 can be configured to communicate with the neuromodulation catheter 110, e.g., via the cable/lead 101. For example, the neuromodulation assembly 120 may further include a sensor (not shown) (e.g., a temperature sensor, a pressure sensor, or a flow rate sensor) and a sensor lead (not shown) (e.g., an electrical lead or a pressure lead) configured to carry a signal from the sensor to the console 102.

In some embodiments, the neuromodulation catheter 110 can include an adapter (not shown) (e.g., a luer lock) configured to be operably coupled to a syringe (not shown). The adapter can be fluidly connected to a lumen (not shown) of the neuromodulation catheter 110, and the syringe can be used, for example, to manually deliver one or more chemicals to the treatment location, to withdraw material from the treatment location, or for another suitable purpose. The syringe can be used in addition to, or in lieu of, the drug pump 104 of the console 102. In still other embodiments, the console 102 may include additional suitable features for delivery of the drugs, agents, and/or chemicals during neuromodulation therapy.

Figure 2:
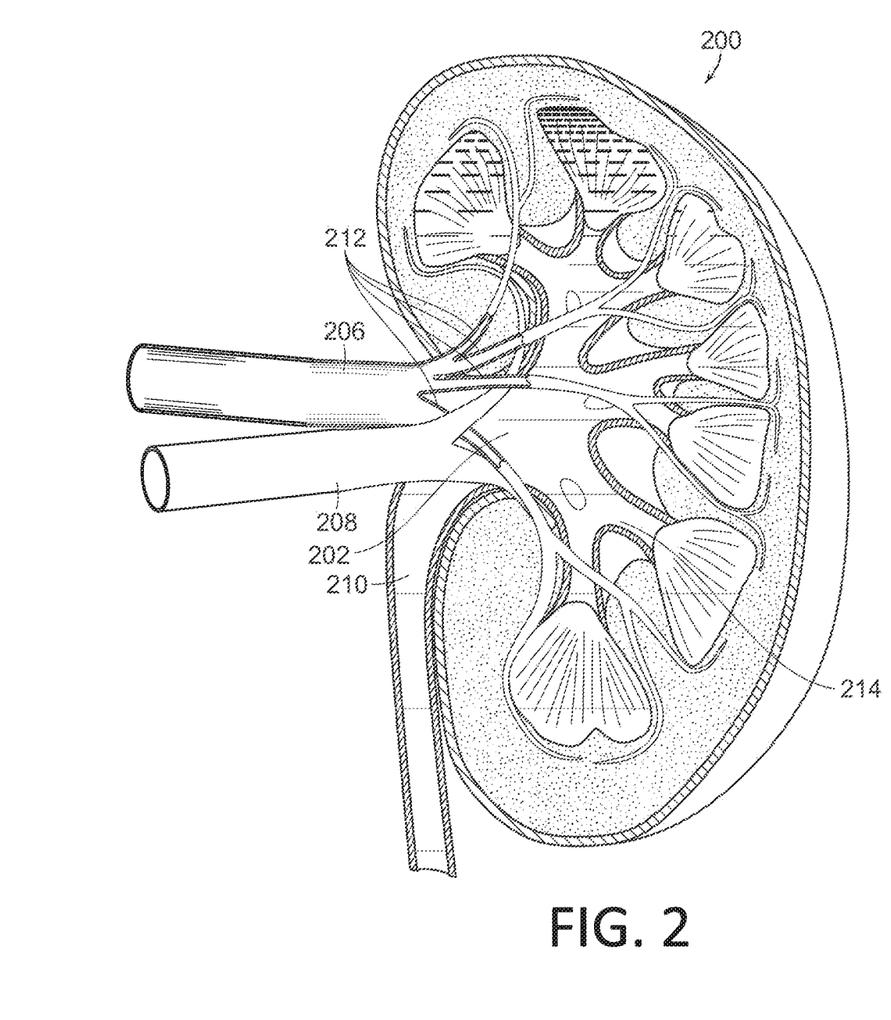
FIG. 2 is a cross-sectional view illustrating a kidney and associated renal anatomy of a human patient.

Selected Examples of Treatment Procedures for Selective Modulation of Afferent Renal Nerves Treatment procedures for selective modulation of renal nerves in accordance with embodiments of the present technology can include applying a selected agent at one or more treatment locations proximate a structure having a relatively-high concentration of afferent renal nerves. In some embodiments, the treatment locations can be proximate or within a kidney of a patient, which can include, for example, the renal pelvis, the ureteropelvic junction, the major calyces, the minor calyces, and/or other suitable structures. FIG. 2, for example, is a cross-sectional view illustrating a kidney 200 including a renal pelvis 202. As shown in FIG. 2, the kidney 200 can further include a renal artery 206, a renal vein 208, and a ureter 210 extending from the renal pelvis 202. The renal artery 206 can branch into a plurality of renal branch arteries 212 of the kidney 200. The renal pelvis 202 can branch into a plurality of calyces 214 (one labeled) of the kidney 200.

As noted previously, a variety of neurotoxic agents may be applied to target regions within the renal anatomy. Suitable agent(s), however, should not induce nephrotoxicity and should have selective neurotoxicity impacting one type of axon but not another. One such agent, capsaicin, can selectively induce toxicity in afferent (sensory) nerves from the periphery to the brain without impacting the efferent or sympathetic population of peripheral nerves innervating the organ. Accordingly, such an agent is expected to sever communication from the kidney to the brain without impacting the sympathetic communication from the brain to the kidney.

Capsaicin is an example of suitable agent for use in accordance with embodiments of the present technology. Capsaicin is an active component of chili peppers, of the genus *Capsicum*, with a molecular formula of $C_{18}H_{27}NO_3$, has a molecular weight of 305.41, and chemical name of 8-Methyl-N-vanillyl-trans-6-nonenamide. Exposure of renal cortical afferent axons to a selective neurotoxic agent, such as capsaicin, is expected to induce local neurotoxicity of exposed axons at their most distal aspect, resulting in progressive loss of axon viability over its entire length.

Figure 3A:
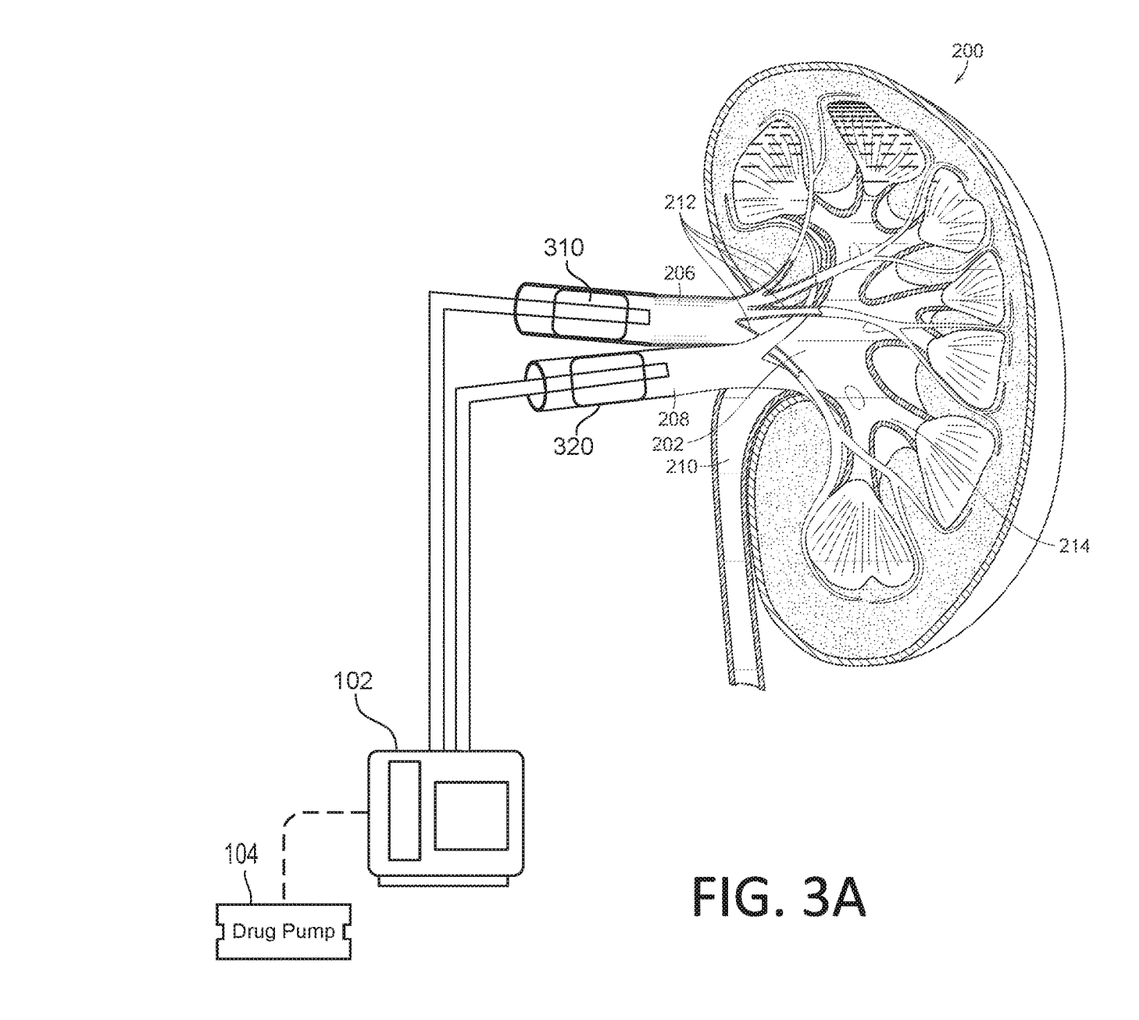
FIG. 3A is a cross-sectional view of the kidney of FIG. 2 and a treatment device including a neuromodulation assembly within the renal vasculature in accordance with an embodiment of the present technology.
Figure 3B:
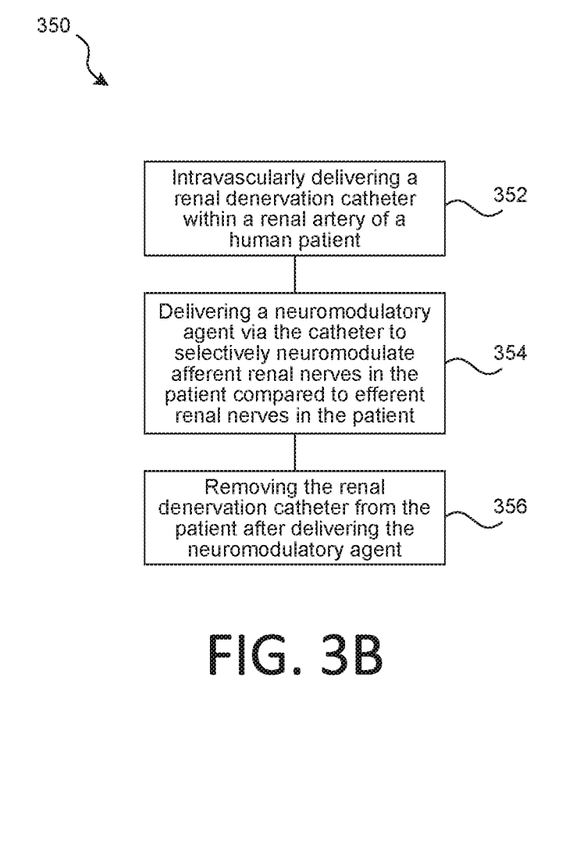
FIG. 3B is a block diagram illustrating a method of for treating a human patient in accordance with some embodiments of the present technology.

Lipophilic agents such as capsaicin, however, are hampered in crossing the renal filtration barrier and gaining access to axons terminating in the renal cortex, thereby preventing local action at the site. However, this local delivery and transport issue can be resolved by covalent coupling of capsaicin or similar agents to lysozyme, an endogenous molecule in many mammalian species that is cleared by renal filtration and which can convey renal-tropic delivery and accumulation to conjugated molecules. Such conjugation may be achieved, for example, using methods known to those of skill in the art, such as amide-based covalent linkage, either directly or by means of an aliphatic linker. Other suitable methods may also be employed, such as disulfide or thioether conjugation. Successful conjugation of capsaicin to a carrier (such as lysozyme or another suitable agent) is also expected to improve aqueous solubility, facilitating administration in a biocompatible aqueous medium.

Once the capsaicin conjugate has been successfully delivered and passed through the glomerulus and into the proximal renal tubule, it can be taken up by the proximal tubular epithelial cells and into the cellular lysosomal compartments where the conjugated capsaicin may be released by hydrolysis or other endogenous degradation pathways, rendering the capsaicin available in the renal parenchyma for the expression of neurotoxic action on the renal afferent nerves. Target afferent nerves having dendritic ends in this area, and as the kidney processes the capsaicin, the target nerves can be selectively affected.

Treatment procedures for selective modulation of afferent renal nerves in accordance with embodiments of the present technology are expected to improve one or more measurable physiological parameters in patients corresponding to systemic sympathetic overactivity or hyperactivity. For example, the treatment procedures are expected to reduce muscle sympathetic nerve activity (e.g., at least about 5%, at least about 10%, etc.) and/or whole body norepinephrine spillover (e.g., at least about 5%, at least about 10%, at least about 15%, at least about 20%, etc.) in patients. These and other clinical effects are expected to be detectable immediately after a treatment procedure or after a delay, e.g., of 1, 2, or 3 months.

Other suitable agents may also be used in embodiments of the present technology. For example, a nanoparticulate emulsion of capsaicin and chitosan may be utilized in some embodiments. Such an emulsion can be directly employed in the treatment procedures described herein. In still further embodiments, other capsaicin-loaded nanocapsules may be utilized.

Example of Treatment Procedures for Selective Modulation of Afferent Renal Nerves Treatment procedures for selective modulation of afferent renal nerves in accordance with embodiments of the present technology can include delivering a selected agent/drug/chemical at one or more treatment locations within the renal vasculature. In some embodiments, for example, the treatment locations can be within portions of the renal artery and/or the renal branch arteries near the renal parenchyma.

As noted previously, one suitable agent for selectively inducing toxicity in afferent renal nerves without negatively impacting the efferent or sympathetic population of peripheral nerves innervating the kidney is capsaicin. While capsaicin has been found in low concentration in the plasma of human experimental subjects following the ingestion of chili peppers without harmful toxicity, systemic vascular administration of large quantities could produce unwanted secondary effects on the physiology of such subjects. Such systemic effects of capsaicin-conjugate administration in effective dosages can be avoided, however, by localized delivery in a renal perfusion loop. FIG. 3A, for example, is a cross-sectional view of the kidney of FIG. 2 and a treatment system 300 configured in accordance with an embodiment of the present technology. The system 300 can include a number of features generally similar or identical to the features of the system 100 of FIG. 1. The treatment system 300 can include, for example, a first catheter 310 having a first assembly 312 intravascularly positioned within the renal artery 206 of the patient, and a second catheter 320 having a distal balloon assembly 322 intravascularly positioned within the renal vein 208 of the patient.

In the illustrated embodiment, the first and second catheters 310 and 320 may comprise balloon catheters with duel lumens (not shown)—one lumen for receiving a guide wire for OTW delivery to the target treatment site within the renal vasculature, and one lumen for a perfusion line. The system 300 can also include a console 302 to which the catheters 310/320 are operably coupled. The console 302 includes a reservoir for containing and cooling a perfusate solution (e.g., Ringers lactate solution or similar solution), a pump for maintaining perfusion, and ports for the administration of the active agent to the patient and clearing and holding the displaced renal blood volume prior to perfusion.

In operation, the system 300 is configured to provide short term isolated perfusion of the kidney 200. After intravascularly positioning the first and second catheters 310 and 320 in the renal artery 206 and renal vein 208, respectively, balloons at a distal region of each catheter are inflated with sufficient pressure to occlude renal blood flow. In patients having one or more accessory arteries, the first catheter 310 may include multiple distal balloons to isolate the kidney 200. The perfusion pump in the console 302 is then activated to flush the blood volume from the isolated kidney 200 into a holding receptacle (not shown). In selected embodiments, the blood volume may be treated with an anti-coagulation agent for re-administration (e.g., approximately 30-40 ml/kidney). The system 300 is then configured to maintain perfusion of the kidney 200 and the capsaicin-conjugate may be administered to the perfusate for renal delivery. Following perfusion (e.g., 5 min), the capsaicin-conjugate may be flushed with a fresh solution of perfusate. The balloons at the distal regions of each catheter 310/320 may then be deflated (allowing normal renal blood flow to resume) and the first catheter 310 and second catheter 320 moved to the contralateral kidney where the procedure is repeated. At conclusion of the perfusion process, the collected blood in the holding receptacle may be re-administered to systemic circulation (if anti-coagulated at the time of collection) and the first and second catheters 310 and 320 removed from the patient to conclude the procedure.

FIG. 3B is a flow diagram of a process or method 350 of detecting and measuring neural electrical signals for evaluating neuromodulation therapy in accordance with embodiments of the present technology. The method 350 can be implemented using the neuromodulation systems described above with reference to FIGS. 1-3A and/or using other suitable systems. Accordingly, for sake of illustration, some features of the method 350 will be described in the context of the embodiments shown in FIGS. 1-3A.

Beginning at block 352, the method 350 includes intravascularly delivering a renal denervation catheter (such as the catheter 310) within a renal artery of the patient and proximate to nerves innervating a kidney of the patient. At block 354, the method 350 can include delivering a neuromodulatory agent via the catheter to selectively neuromodulate afferent renal nerves in the patient compared to efferent renal nerves in the patient. As described herein, for example, in one specific embodiment the neuromodulatory agent may comprise a capsaicin-lysozome conjugate that is delivered to the kidney of the patient, and which selectively modulates afferent renal nerves in the patient compared to efferent renal nerves. At block 356, the method continues by removing the renal denervation catheter from the patient after delivering the neuromodulatory agent to conclude the procedure. In some embodiments, the method 350 can further include repositioning the neuromodulation catheter and/or adjusting one or more parameters for delivery of the neuromodulatory agent.

Renal Neuromodulation

Renal neuromodulation is the partial or complete incapacitation or other effective disruption of nerves of the kidneys (e.g., nerves terminating in the kidneys or in structures closely associated with the kidneys). In particular, renal neuromodulation can include inhibiting, reducing, and/or blocking neural communication along neural fibers (e.g., efferent and/or afferent neural fibers) of the kidneys. Such incapacitation can be long-term (e.g., permanent or for periods of months, years, or decades) or short-term (e.g., for periods of minutes, hours, days, or weeks). Renal neuromodulation is expected to contribute to the systemic reduction of sympathetic tone or drive and/or to benefit at least some specific organs and/or other bodily structures innervated by sympathetic nerves. Accordingly, renal neuromodulation is expected to be useful in treating clinical conditions associated with systemic sympathetic overactivity or hyperactivity, particularly conditions associated with central sympathetic overstimulation. For example, renal neuromodulation is expected to efficaciously treat hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, polycystic ovary syndrome, osteoporosis, erectile dysfunction, and sudden death, among other conditions.

Renal neuromodulation can be electrically-induced, thermally-induced, chemically-induced (as discussed in particular herein), or induced in another suitable manner or combination of manners at one or more suitable target sites during a treatment procedure. The target site can be within or otherwise proximate to a renal lumen (e.g., a renal artery, a ureter, a renal pelvis, a major renal calyx, a minor renal calyx, or another suitable structure), and the treated tissue can include tissue at least proximate to a wall of the renal lumen. Further, as disclosed herein, a treatment procedure can include selectively modulating afferent renal nerves via delivery of one or more chemicals (e.g., drugs or other agents) to tissue at a treatment location in a manner that modulates neural function. As discussed herein, for example, the chemical can be selected to affect the treatment location generally or to selectively affect some structures at the treatment location over other structures.

A variety of suitable techniques can be used to deliver chemicals to tissue at a treatment location. For example, chemicals can be delivered via a perfusion process as described above with reference to FIG. 3A, via simple diffusion through a body lumen wall, electrophoresis, or another suitable mechanism, and/or via one or more needles originating outside the body or within the vasculature or other body lumens. In other embodiments, a chemical can be introduced into tissue at a treatment location using other suitable methods. Similar techniques can be used to introduce chemicals that are not configured to cause neuromodulation, but rather to facilitate neuromodulation via another treatment modality.

Related Anatomy and Physiology

As noted previously, the sympathetic nervous system (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to physiological features as diverse as pupil diameter, gut motility, and urinary output. This response is also known as sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

A. The Sympathetic Chain

Figure 4:
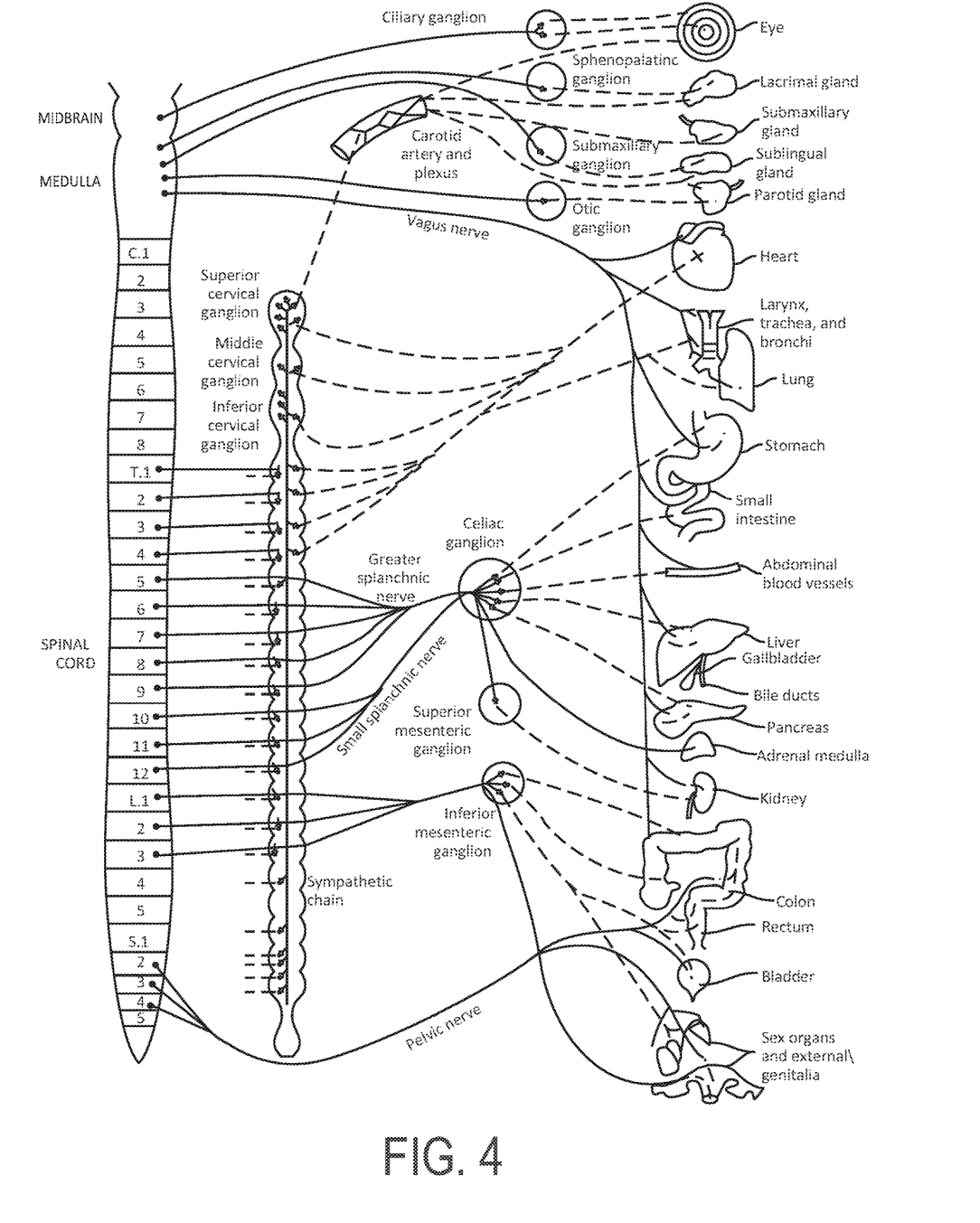
FIG. 4 is a conceptual illustration of the sympathetic nervous system (SNS) and how the brain communicates with the body via the SNS.

As shown in FIG. 4, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia, discussed above. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

1. Innervation of the Kidneys

Figure 5:
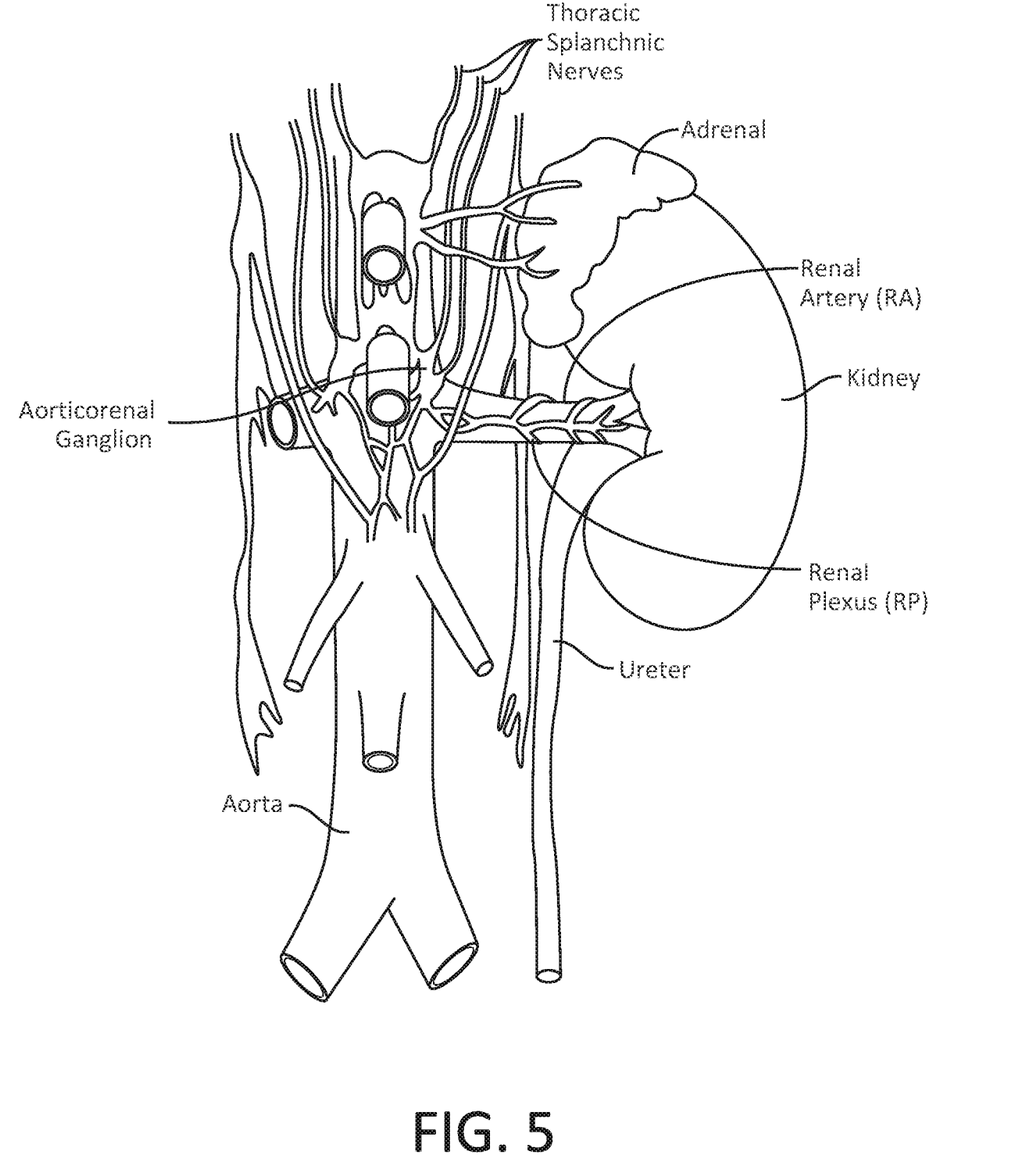
FIG. 5 is an enlarged anatomic view of nerves innervating a left kidney to form the renal plexus surrounding the left renal artery.

As FIG. 5 shows, the kidney is innervated by the renal plexus (RP), which is intimately associated with the renal artery. The renal plexus (RP) is an autonomic plexus that surrounds the renal artery and is embedded within the adventitia of the renal artery. The renal plexus (RP) extends along the renal artery until it arrives at the substance of the kidney. Fibers contributing to the renal plexus (RP) arise from the celiac ganglion, the superior mesenteric ganglion, the aorticorenal ganglion and the aortic plexus. The renal plexus (RP), also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus (RP) and are distributed to the renal vasculature.

2. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well-known adverse consequences of chronic sympathetic over activity, such as hypertension, left ventricular hypertrophy, ventricular arrhythmias, sudden cardiac death, insulin resistance, diabetes, and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium ($Na^+$) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 6:
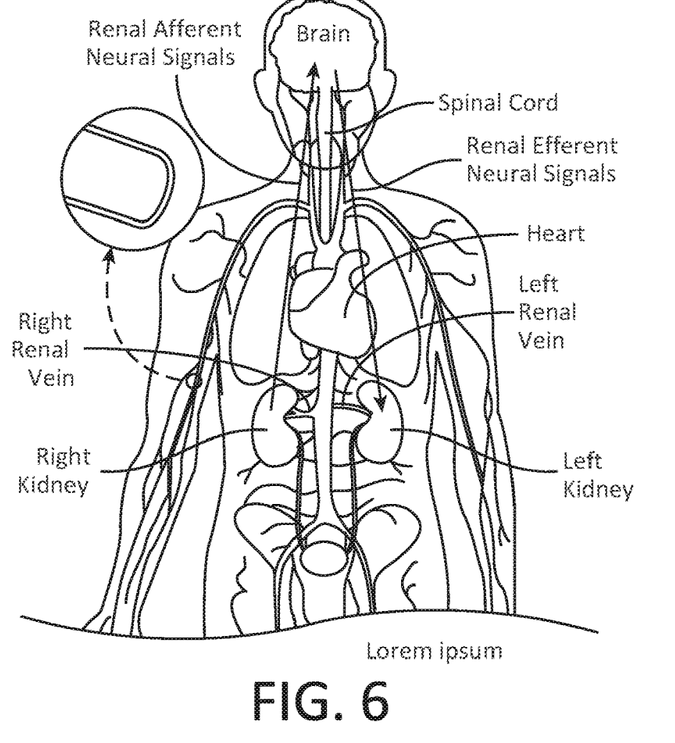
FIGS. 6 and 7 are anatomic and conceptual views, respectively, of a human body depicting neural efferent and afferent communication between the brain and kidneys.
Figure 7:
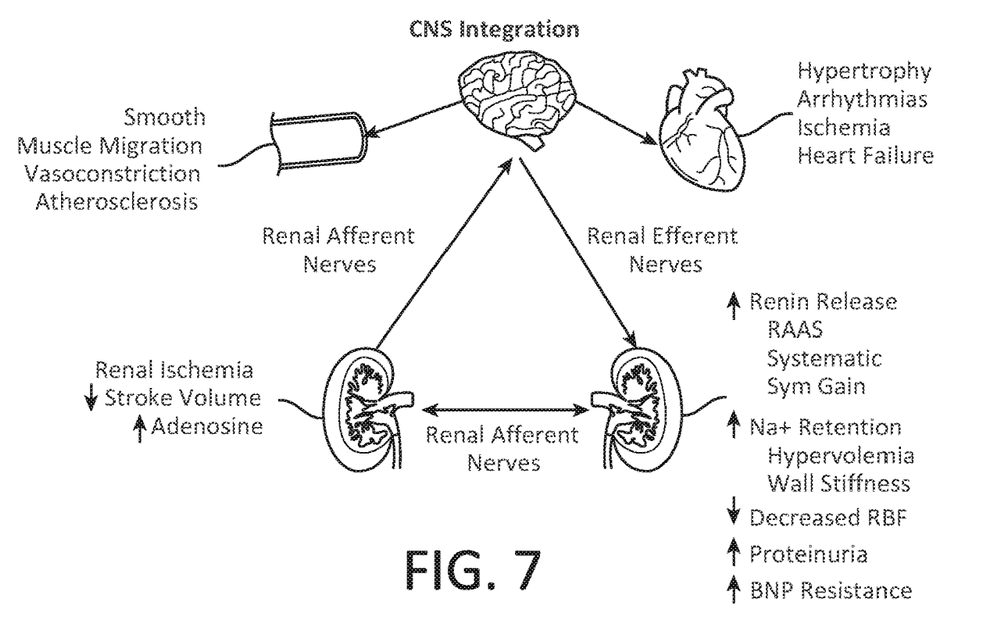

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 6 and 7, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 4. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

C. Achieving Intravascular Access to the Renal Artery

Figures 8, 9:
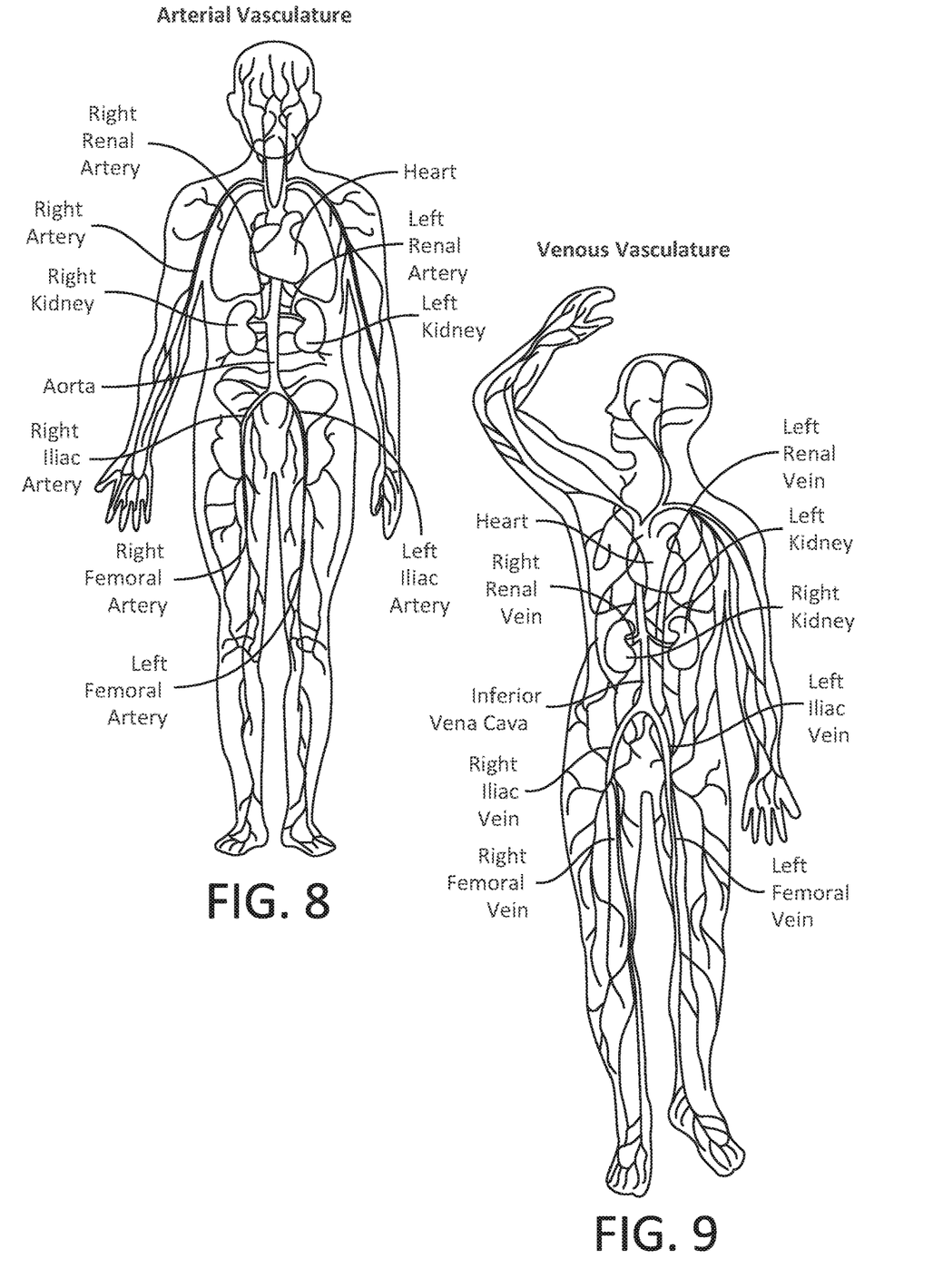
FIGS. 8 and 9 are anatomic views of the arterial vasculature and venous vasculature, respectively, of a human.

In accordance with the present technology, neuromodulation of a left and/or right renal plexus (RP), which is intimately associated with a left and/or right renal artery, may be achieved through intravascular access. As FIG. 8 shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

As FIG. 9 shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

The femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus (RP) may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. For example, navigation can be impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e. cause the wall of the artery to pulse).

Even after accessing a renal artery and facilitating stable contact between neuromodulatory apparatus and a luminal surface of the artery, nerves in and around the adventia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, a full-circle lesion likely resulting from a continuous circumferential treatment may be potentially related to renal artery stenosis. Therefore, the formation of more complex lesions along a longitudinal dimension of the renal artery and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time should be avoided because to prevent injury to the kidney such as ischemia. It could be beneficial to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal connectivity of blood flow past a vessel wall treatment site and/or radiative heat transfer; (e) renal artery motion relative to the aorta induced by respiration, patient movement, and/or blood flow pulsatility; and (f) the take-off angle of a renal artery relative to the aorta. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery should conform to the geometry of the artery. Renal artery vessel diameter, DRA, typically is in a range of about 2-10 mm, with most of the patient population having a DRA of about 4 mm to about 8 mm and an average of about 6 mm.

Renal artery vessel length, LRA, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

An additional property of the renal artery that may be of interest is the degree of renal motion relative to the aorta induced by respiration and/or blood flow pulsatility. A patient's kidney, which is located at the distal end of the renal artery, may move as much as 4" cranially with respiratory excursion. This may impart significant motion to the renal artery connecting the aorta and the kidney, thereby requiring from the neuromodulatory apparatus a unique balance of stiffness and flexibility to maintain contact between the energy delivery element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Moreover, the various embodiments described herein may also be combined to provide further embodiments. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment.

Certain aspects of the present technology may take the form of computer-executable instructions, including routines executed by a controller or other data processor. In some embodiments, a controller or other data processor is specifically programmed, configured, and/or constructed to perform one or more of these computer-executable instructions. Furthermore, some aspects of the present technology may take the form of data (e.g., non-transitory data) stored or distributed on computer-readable media, including magnetic or optically readable and/or removable computer discs as well as media distributed electronically over networks. Accordingly, data structures and transmissions of data particular to aspects of the present technology are encompassed within the scope of the present technology. The present technology also encompasses methods of both programming computer-readable media to perform particular steps and executing the steps.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. Directional terms, such as "upper," "lower," "front," "back," "vertical," and "horizontal," may be used herein to express and clarify the relationship between various elements. It should be understood that such terms do not denote absolute orientation. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. A method comprising:
intravascularly positioning a first catheter comprising a first expandable member within a renal artery of a patient;
intravascularly positioning a second catheter comprising a second expandable member within a renal vein of the patient, wherein the renal artery and the renal vein are connected to a kidney of the patient;
expanding the first expandable member to substantially occlude blood flow through the renal artery;
expanding the second expandable member to substantially occlude blood flow through the renal vein;
perfusing a perfusate solution through the kidney of the patient; and
administering a neuromodulatory agent through the kidney via at least one of the first catheter or the second catheter to neuromodulate renal nerves in the patient, wherein the neuromodulatory agent comprises a lipophilic agent coupled to an endogenous carrier molecule, and wherein administering the neuromodulatory agent comprises introducing the neuromodulatory agent to the perfusate solution.

2. The method of claim 1, wherein the lipophilic agent coupled to the endogenous carrier molecule comprises a capsaicin conjugate.

3. The method of claim 2, wherein the capsaicin conjugate comprises a capsaicin-lysozyme conjugate.

4. The method of claim 1, further comprising, after expanding the first expandable member and the second expandable member and prior to perfusing the perfusate solution through the kidney, flushing blood from the kidney.

5. The method of claim 4, further comprising, after introducing the neuromodulatory agent to the perfusate solution, readministering the blood to systemic circulation.

6. The method of claim 1, further comprising, after administering the neuromodulatory agent through the kidney, flushing the neuromodulatory agent from the kidney.

7. The method of claim 1, further comprising, after administering the neuromodulatory agent through the kidney, removing the first catheter and the second catheter from the patient.

8. The method of claim 1, wherein administering the neuromodulatory agent through the kidney via at least one of the first catheter or the second catheter to neuromodulate renal nerves in the patient selectively neuromodulates afferent renal nerves in the patient compared to efferent renal nerves in the patient.

9. The method of claim 1, wherein at least one of the first expandable member or the second expandable member comprises a balloon.

10. The method of claim 1,
wherein the renal artery is a first renal artery, wherein the first catheter comprises a third expandable member, and
wherein the method further comprises positioning the third expandable member in an accessory renal artery of the patient and expanding the third expandable member to substantially occlude blood flow through the accessory renal artery.

11. The method of claim 1, wherein the renal artery is a first renal artery, the renal vein is a first renal vein, and the kidney is a first kidney, the method further comprising:
intravascularly positioning the first catheter comprising the first expandable member within a second renal artery of the patient;
intravascularly positioning the second catheter comprising the second expandable member within a second renal vein of the patient, wherein the second renal artery and the second renal vein are connected to a second kidney of the patient;
expanding the first expandable member to substantially occlude blood flow through the second renal artery;
expanding the second expandable member to substantially occlude blood flow through the second renal vein; and
administering the neuromodulatory agent through the second kidney via at least one of the first catheter or the second catheter to neuromodulate renal nerves in the patient.

12. The method of claim 1, wherein the neuromodulatory agent selectively induces toxicity in afferent renal nerves without impacting efferent renal nerves in the patient.

13. The method of claim 1, wherein administering the neuromodulatory agent selectively blocks neural signaling along afferent renal nerves of the patient.

14. The method of claim 1, wherein administering the neuromodulatory agent results in a therapeutically beneficial reduction in blood pressure of the patient.

15. The method of claim 1, wherein intravascularly positioning the first catheter within the renal artery comprises delivering the first catheter over a guidewire.

16. The method of claim 1, wherein administering the neuromodulatory agent through the kidney via at least one of the first catheter or the second catheter to neuromodulate renal nerves in the patient nerves improves a measurable physiological parameter in the patient corresponding to systemic sympathetic overactivity or hyperactivity.

17. The method of claim 1, wherein administering the neuromodulatory agent through the kidney via at least one of the first catheter or the second catheter to neuromodulate renal nerves in the patient nerves reduces whole body norepinephrine spillover in the patient.

18. The method of claim 1, wherein administering the neuromodulatory agent through the kidney via at least one of the first catheter or the second catheter to neuromodulate renal nerves in the patient nerves reduces muscle sympathetic nerve activity in the patient.

19. The method of claim 1, wherein the neuromodulatory agent neuromodulates renal nerves of a renal parenchyma of the kidney of the patient.

20. The method of claim 19, wherein the neuromodulatory agent passes through a glomerulus of the renal parenchyma and into a proximal renal tubule of the renal parenchyma.

* * * * *